US009956126B2

(12) United States Patent
Russell

(10) Patent No.: US 9,956,126 B2
(45) Date of Patent: May 1, 2018

(54) METHOD OF TRANSPORTING A PATIENT

(71) Applicant: The Boeing Company, Chicago, IL (US)

(72) Inventor: Rex Alan Russell, Wallingford, PA (US)

(73) Assignee: The Boeing Company, Chicago, IL (US)

(*) Notice: Subject to any disclaimer, the term of this patent is extended or adjusted under 35 U.S.C. 154(b) by 402 days.

(21) Appl. No.: 14/677,802

(22) Filed: Apr. 2, 2015

(65) Prior Publication Data

US 2015/0209203 A1 Jul. 30, 2015

Related U.S. Application Data

(62) Division of application No. 13/420,781, filed on Mar. 15, 2012, now Pat. No. 9,022,263.

(51) Int. Cl.
*A01K 65/00* (2006.01)
*A61G 3/00* (2006.01)
*A61G 3/08* (2006.01)
*A61F 5/37* (2006.01)
*A61G 5/00* (2006.01)

(52) U.S. Cl.
CPC .............. *A61G 3/00* (2013.01); *A61F 5/3769* (2013.01); *A61G 3/003* (2013.01); *A61G 3/0858* (2013.01); *A61G 5/00* (2013.01); *A61G 2220/10* (2013.01)

(58) Field of Classification Search
CPC ......... A61G 3/00; A61G 3/003; A61G 3/0858
See application file for complete search history.

(56) References Cited

U.S. PATENT DOCUMENTS

| 245,602 A | 8/1881 | Barton |
| 2,229,483 A * | 1/1941 | Toulmin Jr. ............ A61G 21/00 296/16 |
| 4,115,884 A | 9/1978 | Keogh |
| 4,210,355 A | 7/1980 | Legueu |
| 4,425,978 A | 1/1984 | Star |
| 4,957,121 A | 9/1990 | Icenogle et al. |
| 5,026,006 A * | 6/1991 | Tinder ................... B64D 25/00 244/118.5 |
| 5,372,396 A | 12/1994 | Van Nahmen |
| 5,490,703 A * | 2/1996 | Hewko ................ A61G 1/0293 244/118.6 |
| 5,615,848 A | 4/1997 | Ceriani |
| 5,702,142 A | 12/1997 | Newell |
| 5,755,479 A | 5/1998 | Lavin et al. |
| 5,779,296 A | 7/1998 | Hewko |
| 5,785,277 A * | 7/1998 | Manning ................. A61G 3/00 244/118.6 |

(Continued)

OTHER PUBLICATIONS

AAR Mobility Systems, "463L Air Cargo Pallet HCU-6/E" retrieved on Mar. 9, 2012.

*Primary Examiner* — Derek Battisti

(57) ABSTRACT

A method of transporting a patient may include providing a medical pod having a pallet forming a floor structure and including sidewalls extending upwardly from the pallet to a roof section to form a container. The method may additionally include coupling a patient restraint system to the floor structure using a transport system located on the floor structure, and moving the patient restraint system from a first position to a second position using the transport system.

20 Claims, 15 Drawing Sheets

(56) References Cited

U.S. PATENT DOCUMENTS

| | | | | |
|---|---|---|---|---|
| 6,273,366 B1 | * | 8/2001 | Sprenger | A61G 3/00 244/118.1 |
| 6,585,188 B2 | * | 7/2003 | Alli | A61G 1/06 244/118.5 |
| 6,923,606 B2 | | 8/2005 | Fehrle et al. | |
| 7,530,403 B2 | | 5/2009 | Cano | |
| 7,946,530 B1 | * | 5/2011 | Talmage, Jr. | B64C 27/006 244/118.2 |
| 8,336,939 B2 | * | 12/2012 | Green | A61G 1/0212 296/20 |
| 2005/0177948 A1 | * | 8/2005 | Hillberry | A61G 1/06 5/662 |
| 2011/0260482 A1 | * | 10/2011 | Bourgraf | A61G 3/00 296/19 |
| 2013/0133317 A1 | * | 5/2013 | Zumbrum | A61G 3/006 60/325 |

* cited by examiner

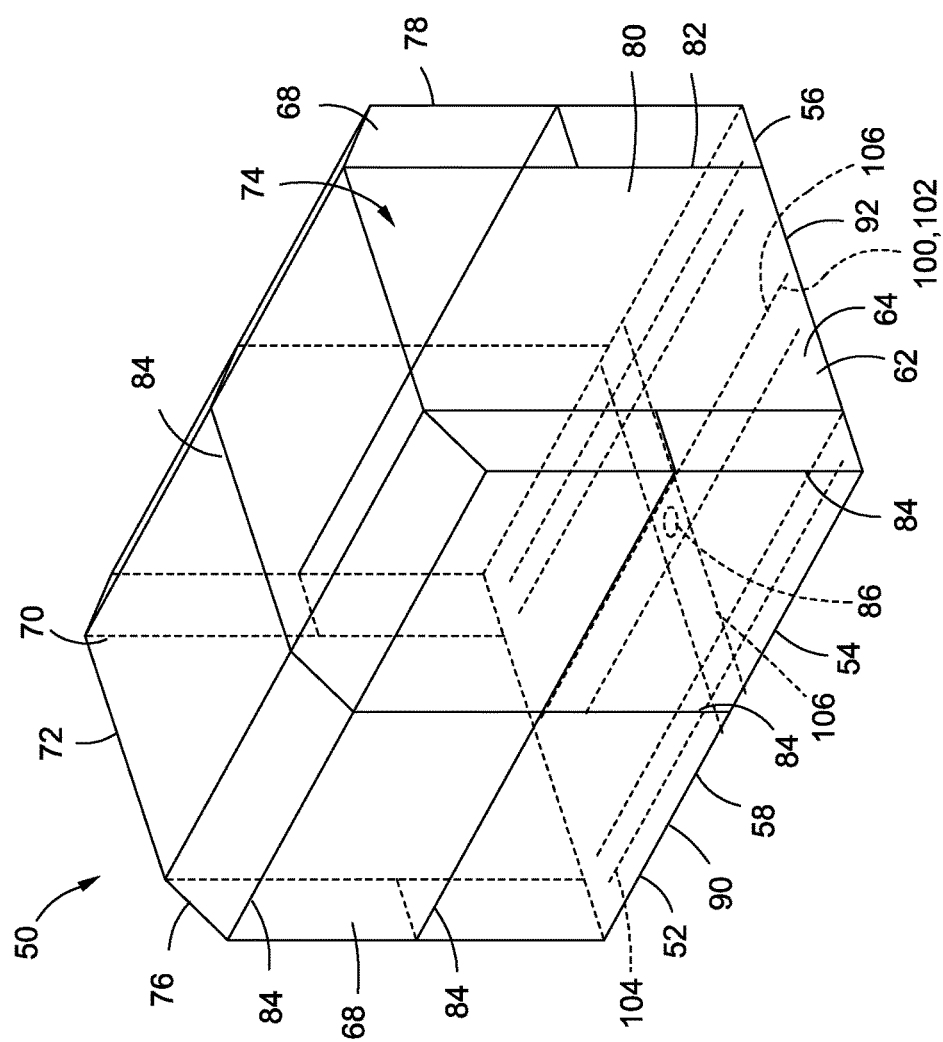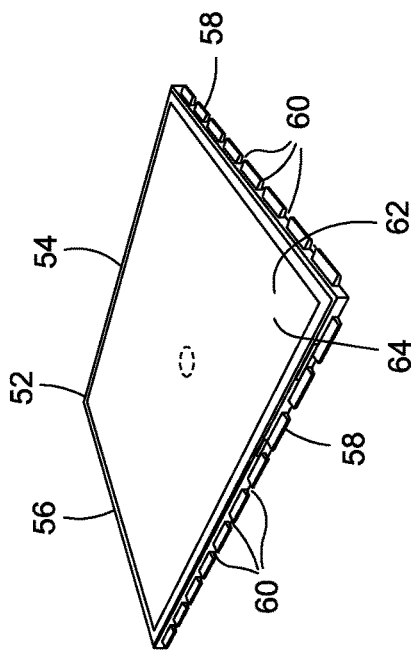

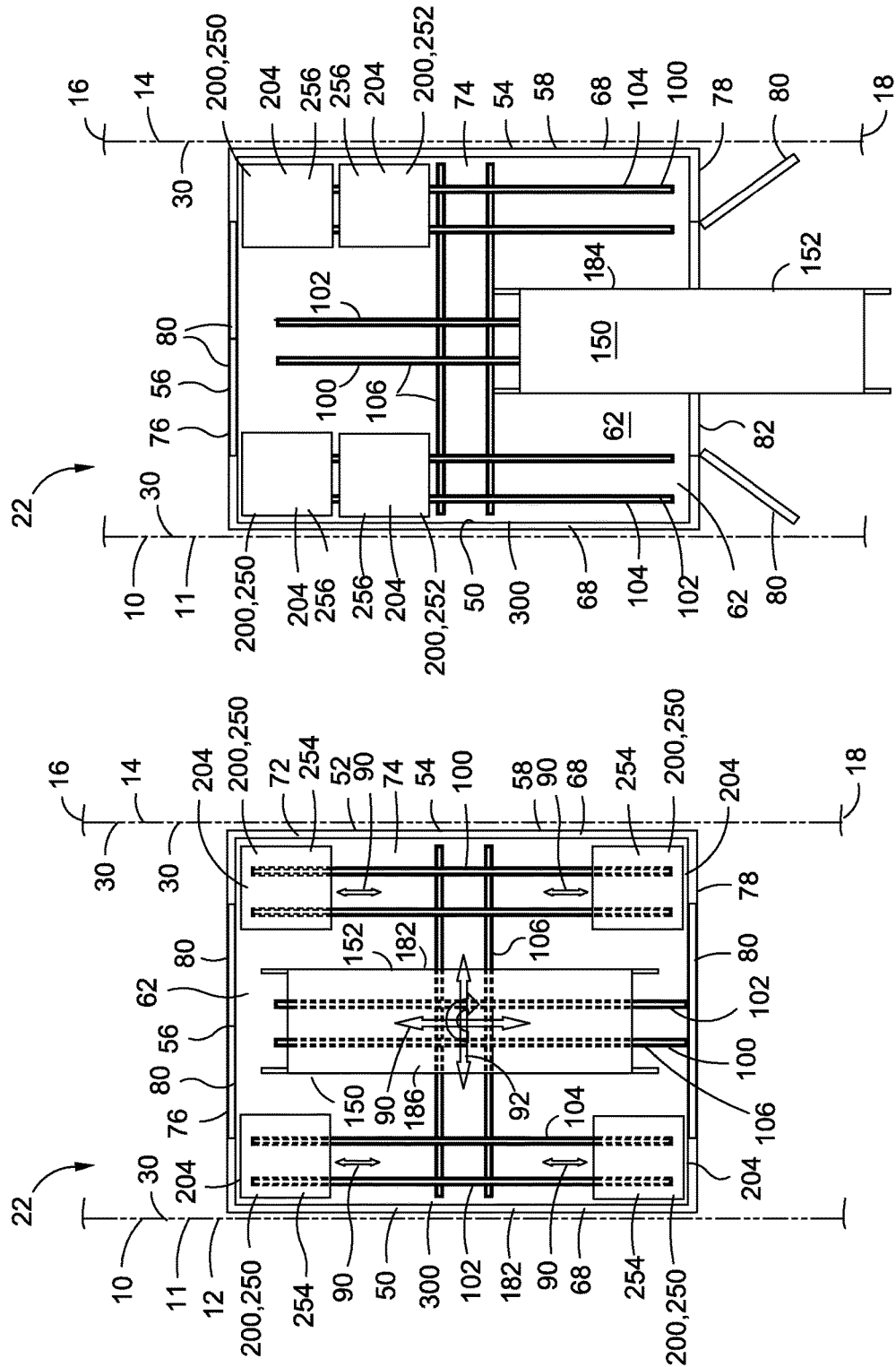

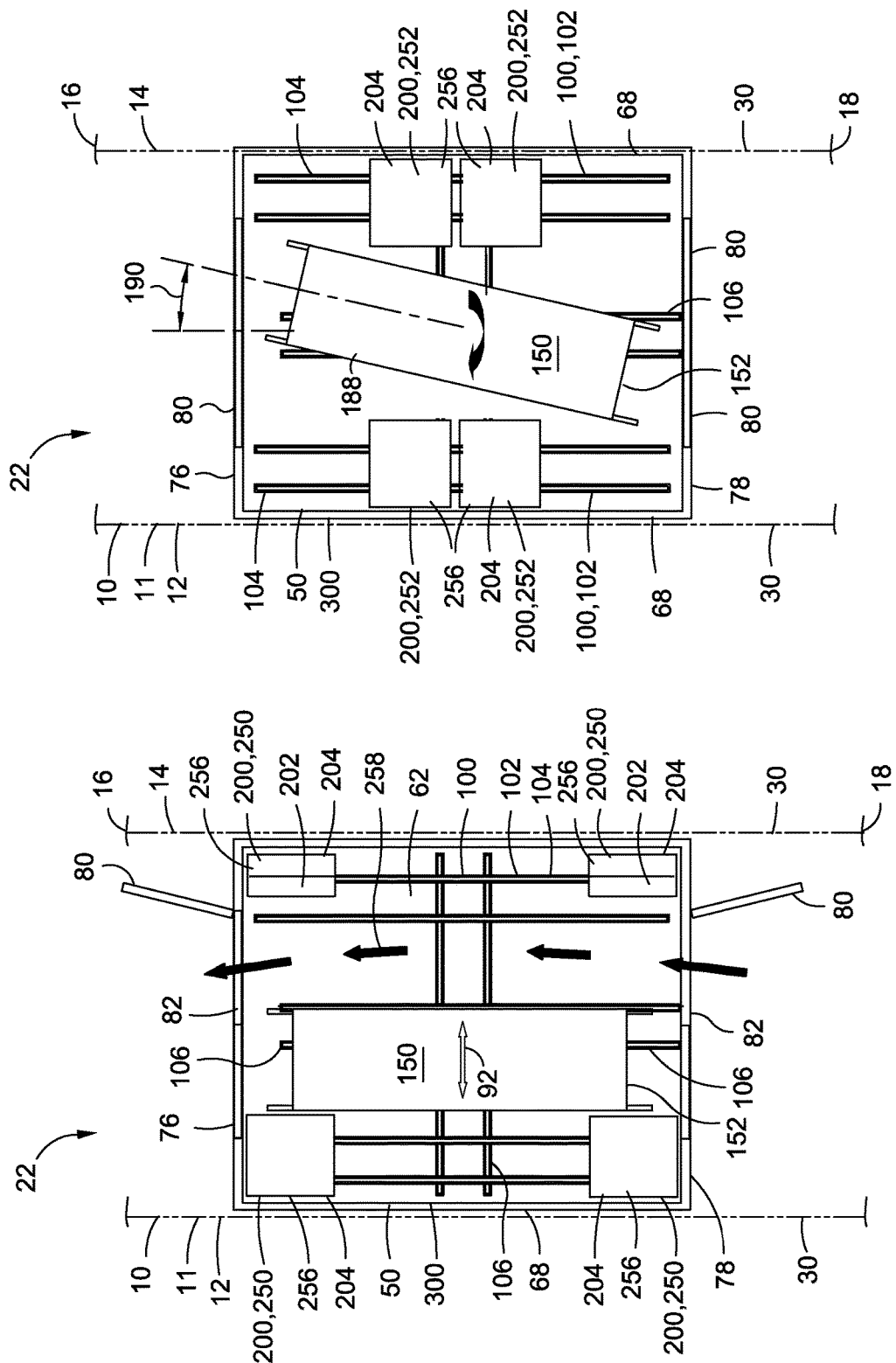

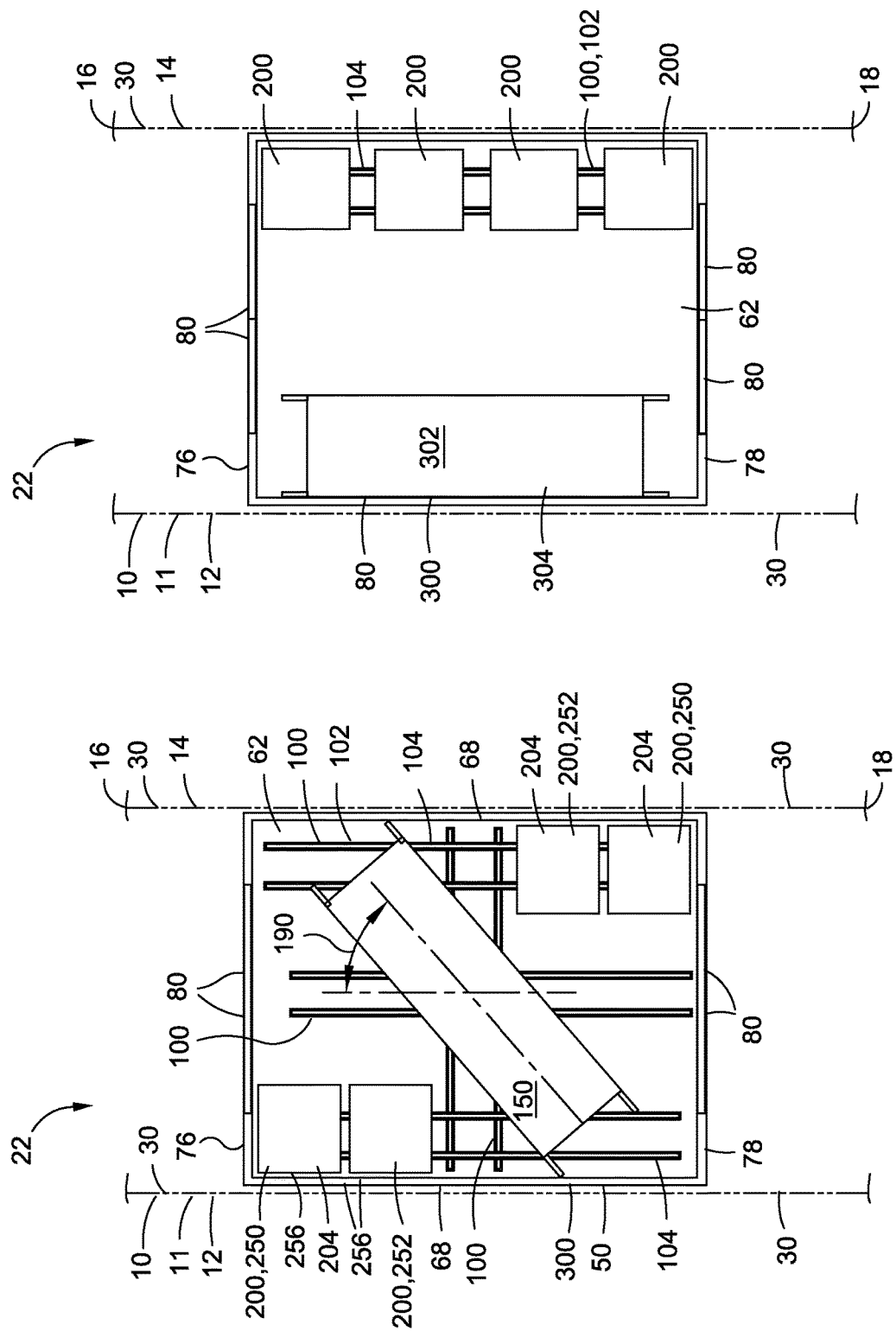

METHOD OF TRANSPORTING A PATIENT

CROSS-REFERENCE TO RELATED APPLICATIONS

The present application is a divisional application of and claims priority to pending U.S. application Ser. No. 13/420,781 filed on Mar. 15, 2012, and entitled PATIENT TRANSPORT POD AND METHOD OF USE, the entire contents of which is expressly incorporated by reference herein.

FIELD

The present disclosure relates generally to patient transport systems and, more particularly, to systems and methods for transporting patients in a vehicle such as an aircraft.

BACKGROUND

Evacuation of wounded personnel such as from a combat zone may conventionally include loading patients (e.g., wounded personnel) into an aircraft such as a helicopter and airlifting the patients to a treatment center. Unfortunately, such conventional means for airlifting patients in aircraft not specifically modified for medical evacuation suffers from several drawbacks. For example, patients are typically carried on a stretcher into the cargo area of the aircraft and the stretcher is then placed on the cargo area floor. Medical personnel must crouch down or kneel down on the floor around the patent in order to examine and treat the patient. The patient and the medical personnel are typically not secured to the aircraft such that turbulence, abrupt maneuvering, or a relatively hard landing of the aircraft may result in the patient and medical personnel impacting interior elements of the cargo area and/or impacting one another.

A further drawback associated with conventional means for evacuating patients is that any specialized medical equipment that is required for treating the patient must be carried onto the aircraft by the medical personnel. The specialized equipment must then be secured against movement by attaching the equipment to the walls of the cargo area. An additional drawback associated with convention evacuation of patients is that the cargo area of an aircraft is typically not outfitted with extensive lighting. In low-visibility conditions such as at night, medical personnel must typically wear headlamps in order to treat the patient.

Another drawback associated with conventional patient evacuation is the relatively high noise level in the cargo area of an aircraft which may hinder communication. Although medical personnel may have personal communication devices with headphones and microphones that allow communication with one another, the patient may not have access to a compatible communication device such that the relatively high noise level in the cargo area may prevent effective communication between the medical personnel and the patient. An additional drawback associated with conventional patient evacuation is that the stretcher holding the patient typically and the cargo area of an aircraft may lack a means for containing bodily fluids from wounded personnel. Such bodily fluids present a biological hazard to the passengers and flight crew of the aircraft. In addition, such bodily fluids present a significant corrosion hazard to the aircraft structure.

As can be seen, there exists a need in the art for a system and method for transporting a medical patient in a vehicle such as an aircraft wherein the patient and medical personnel are secured against harmful movement. In addition, there exists a need in the art for a system and method for transporting a medical patient that avoids the need for medical personnel to hand-carry specialized medical equipment on board the aircraft. Furthermore, there exists a need in the art for a system and method for transporting a medical patient that provides a relatively well lit and relatively quiet environment for examining and treating the patient.

SUMMARY

The above-noted needs associated with patient evacuation are specifically addressed and alleviated by the present disclosure which provides a medical pod for a vehicle. The medical pod may include a pallet having an upper surface defining a floor structure. A plurality of side walls may extend upwardly from the pallet and may be connected to a roof section to form a container configured to be loaded and unloaded into a vehicle. The medical pod may include a transport system located on the floor structure of the container. A patient restraint system may be positioned within the container and may have a patient support structure that may be coupled to the transport system such that the patient restraint system is movable relative to the floor structure.

In a further embodiment, disclosed is a medical pod which may include a pallet configured to be loaded and unloaded into a cargo area or an aircraft. The pallet may include an upper surface defining a floor structure. A plurality of side walls may extend upwardly from the pallet and may be connected to a roof section to form a container. The medical pod may include a transport system located on the floor structure. The medical pod may further include a seat having a seat support structure coupled to the transport system and being configured to enable translation and rotation of the seat relative to the floor structure. A patient restraint system may be positioned within the container and may have a patient support structure that may be coupled to the transport system such that the patient restraint system is translatable and rotatable relative to the floor structure.

Also disclosed is a method of transporting a patient which may include the step of providing a medical pod having a pallet forming a floor structure and including sidewalls extending upwardly from the pallet to a roof section to form a container. The method may further include coupling a patient restraint system to the floor structure using a transport system located on the floor structure. In addition, the method may include moving the patient restraint system from a first position to a second position using the transport system.

The features, functions and advantages that have been discussed can be achieved independently in various embodiments of the present disclosure or may be combined in yet other embodiments, further details of which can be seen with reference to the following description and drawings below.

BRIEF DESCRIPTION OF THE DRAWINGS

These and other features of the present disclosure will become more apparent upon reference to the drawings wherein like numbers refer to like parts throughout and wherein:

FIG. 4 is a perspective illustration of a container comprised of a pallet and a plurality of pod side walls extending toward a roof section to collectively enclose the container;

FIG. 5 is a perspective illustration of a pallet having side rails with a plurality of detents for receiving rail locks of a cargo handling system of the aircraft;

FIG. 12 is a top schematic view of an embodiment of the medical pod illustrating the movement capability of the patient restraint system and the seats;

FIG. 13 is a top schematic view of an embodiment of the medical pod illustrating translation of the patient restraint system along a longitudinal direction to a position at least partially outside of the container;

FIG. 14 is a top schematic view of an embodiment of the medical pod illustrating translation of the patient restraint system along a lateral direction toward a side of the container to provide a passageway for passenger or personnel for the medical pod;

FIG. 15 is a top schematic view of an embodiment of the medical pod illustrating rotation of the patient restraint system;

FIG. 16 is a top schematic view of an embodiment of medical pod illustrating the patient restraint system rotated into an orientation of approximately 45° relative to the longitudinal axis of the container;

FIG. 17 is a top schematic view of an embodiment of the medical pod having a stack of stretchers mounted to one of the pod side walls;

DETAILED DESCRIPTION

Figure 1:
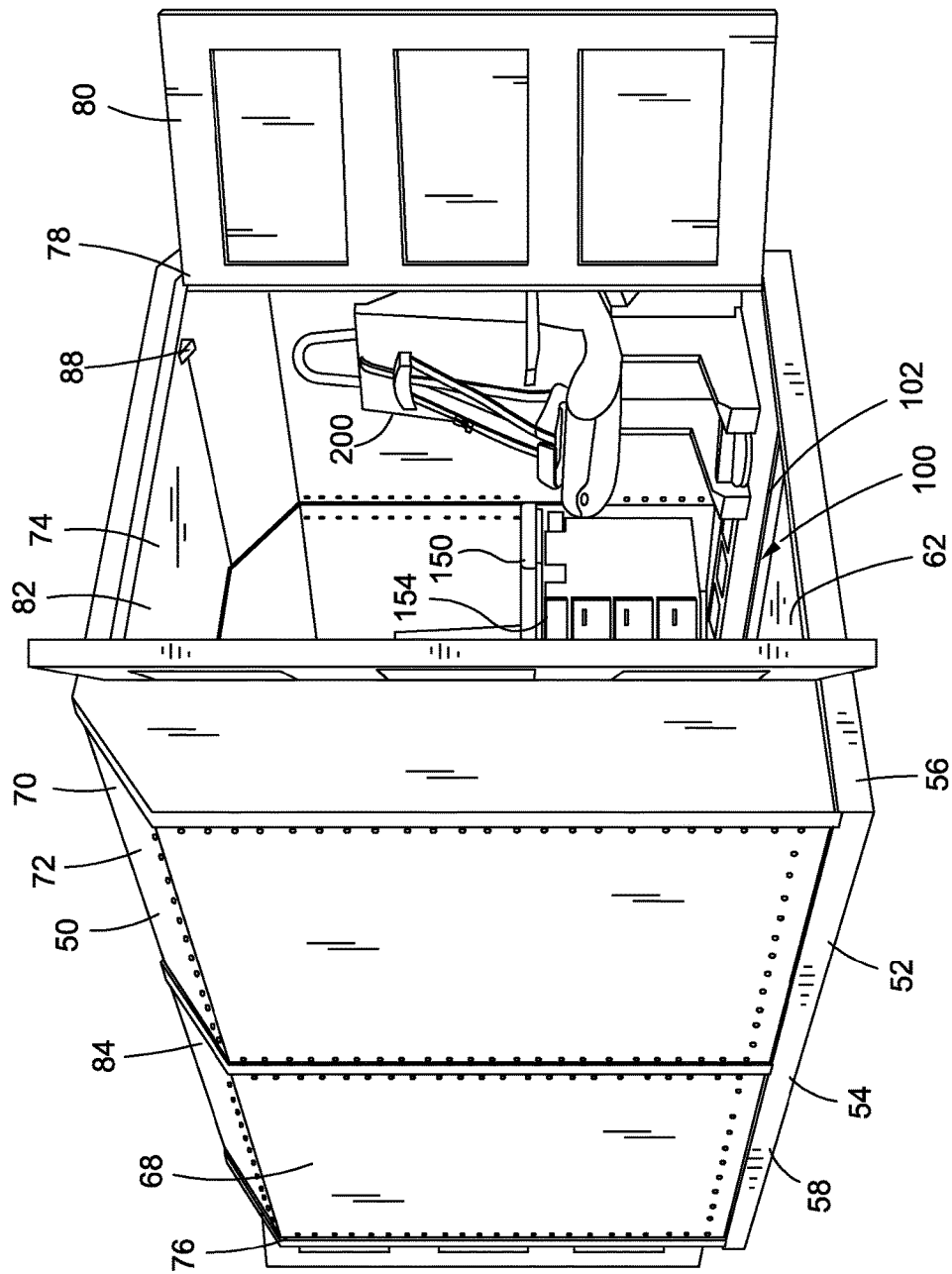
FIG. 1 is a perspective illustration of a medical pod such as for an aircraft.
Figure 2:
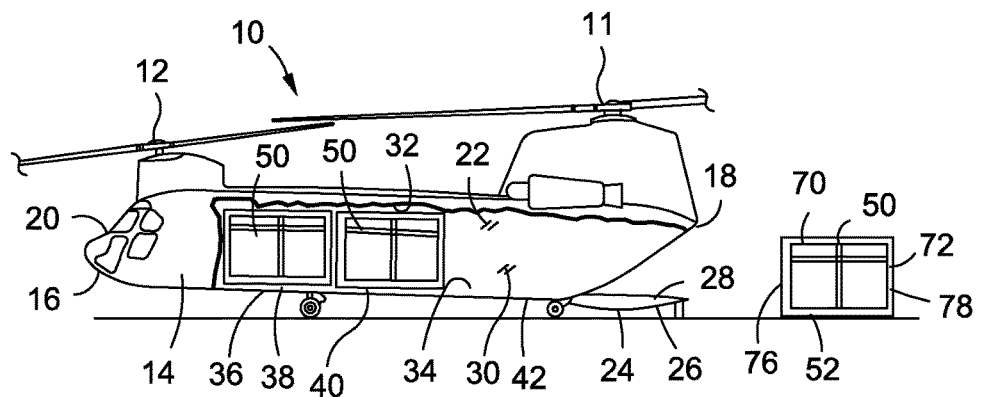
FIG. 2 is a partially cutaway side view of a rotorcraft illustrating a plurality of medical pods loaded into a cargo area of the rotorcraft.

Referring now to the drawings wherein the showings are for purposes of illustrating preferred and various embodiments of the disclosure, shown in FIG. 1 is a perspective illustration of a medical pod 50 which may be loaded into a vehicle 10 (FIG. 2) such as an aircraft 11 (FIG. 2) such as a rotorcraft 12 (FIG. 2). In an embodiment, the medical pod 50 may be sized and configured to fit within the cargo area 22 (FIG. 2) of an aircraft 11 for performing medical evacuations of wounded personnel or other patients. The medical pod 50 may include a container 72 that may be secured to the aircraft 11. The container 72 may contain a patient restraint system 150 including a patient table 154 for securely supporting a patient. The container 72 may also include a plurality of seats 200 for supporting and securing medical personnel to the aircraft. The patient restraint system 150 and the seats 200 (FIG. 8) may be coupled to the container 72 such that the patient and medical personnel are restrained against harmful movement in the event of turbulence, an abrupt maneuver, and/or a hard landing of the aircraft 11.

Figure 8:
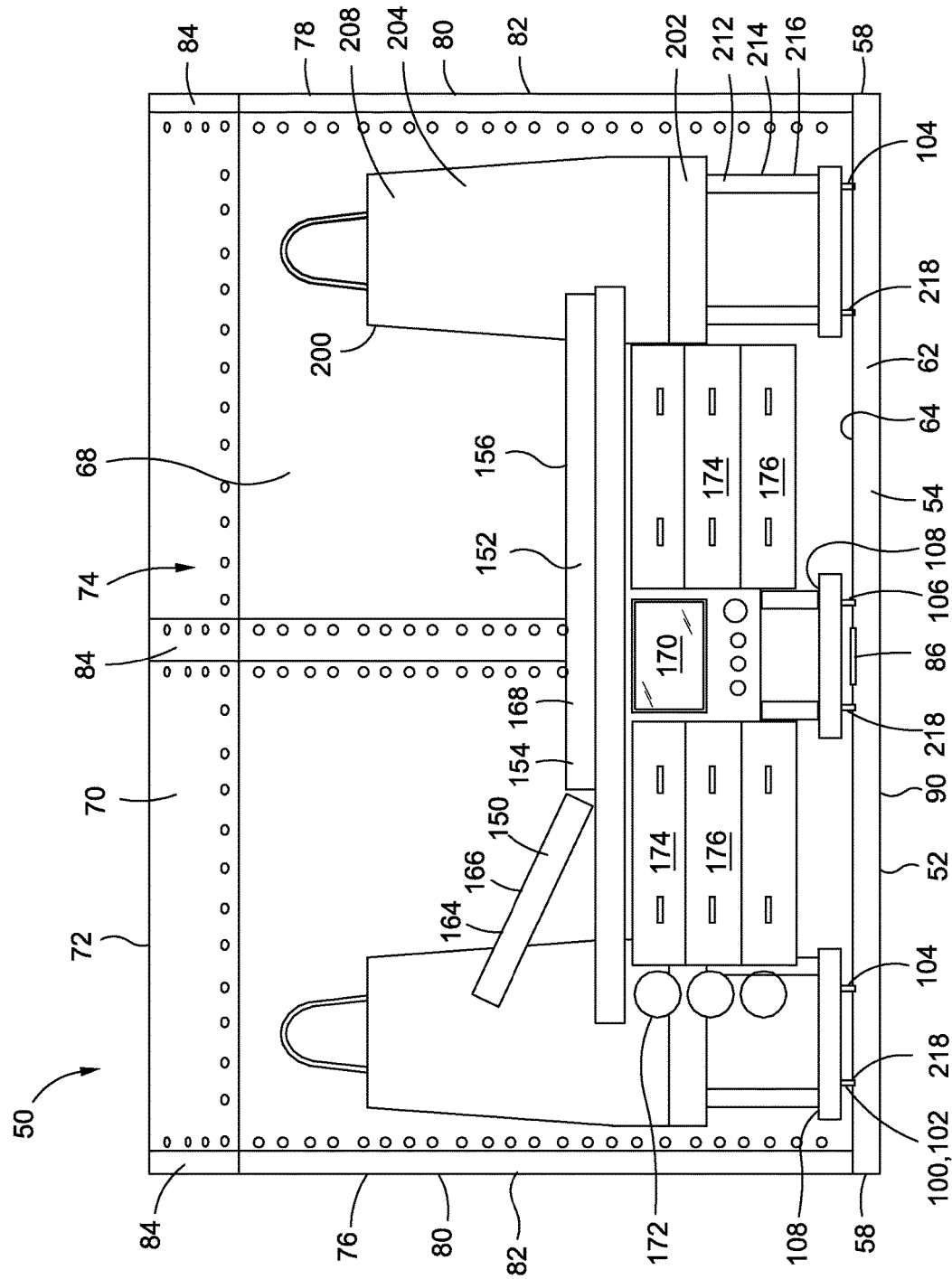
FIG. 8 is a side view of the container.

Advantageously, the medical pod 50 may be provided as a dedicated, self-contained unit wherein medical personnel may treat a patient in a quiet, well-lit environment using specialized medical equipment 170 (FIG. 8) that may be furnished with the medical pod 50. Although the patient restraint system 150 and the seats 200 (FIG. 8) may be coupled to the container, the patient restraint system 150 and/or the seats 200 may be movable within the container 72 while maintaining secure attachment to the floor structure 62 (FIG. 8). In this manner, the patient restraint system 150 and the seats 200 may be maneuvered and locked into a desired position and/or orientation to provide medical personnel with access to area(s) of the patient's body requiring medical attention. Additionally, the patient restraint system 150 and/or the seats 200 may be maneuvered into a position that provides a passageway 258 (FIG. 14) for individuals to pass through the container 72.

Referring to FIG. 1, the container 72 may be provided in a generally orthogonal shape having beveled upper corners such that the container is shaped complementary to the geometry of the cargo area 22 (FIG. 2) of an aircraft 11 (FIG. 2) such as a rotorcraft 12. The base of the container 72 may comprise a pallet 52 having an upper surface 64 (FIG. 4) which may define a floor structure 62 for the medical pod 50. The container 72 may include a plurality of pod side walls 68 that may extend upwardly from the pallet 52 and may be interconnected to a roof section 70. The container 72 may include doors 80 on the forward and/or aft end 76, 78 of the container 72. Although each end 76, 78 is shown as having a pair of doors 80 that swing open away from one another, the door(s) may be provided in any configuration, without limitation, and may include a single door, a rolling door which may roll up vertically into the container interior 74, or any other door configuration.

Shown in FIG. 2 is a rotorcraft 12 with the fuselage 14 partially cutaway to illustrate a pair of medical pods 50 loaded into the cargo area 22 in end-to-end arrangement. In such an arrangement, the doors 80 of the adjoining ends of the medical pod 50 may be omitted to allow an individual to pass from one medical pod 50 into an adjacent medical pod 50. In addition, the door(s) of the forward-most medical pods 50 may be sized and configured complementary to a door of a cockpit 20 at a forward end 16 of the aircraft 11 to allow the flight crew to pass through the medical pod 50 from the cockpit 20. Each one of the medical pods 50 may be sized and configured to be secured to the aircraft 11 (e.g., rotorcraft 12) at a predetermined pallet position 36 in the cargo area 22 as described in greater detail below. For example, in FIG. 2, a pair of medical pods 50 may be installed in first and second pallet 52 positions 38, 40 of the cargo area 22. A third medical pod 50 is shown located outside of the rotorcraft 12 awaiting loading through the cargo door 24 to be positioned in a third pallet position 42 of the cargo area 22 toward the aft end 18 of the rotorcraft 12. Although FIG. 2 illustrates an arrangement wherein three (3) of the medical pods 50 may be loaded into the cargo area 22 of the rotorcraft 12, the medical pods 50 may be sized and configured to allow for installation of a predetermined quantity of medical pods 50 for a given aircraft configuration. In this regard, the medical pod 50 as disclosed herein may be provided in any length, width, and/or height, without limitation, and is not necessarily dictated by the size and configuration of a given aircraft cargo area.

Figure 3:
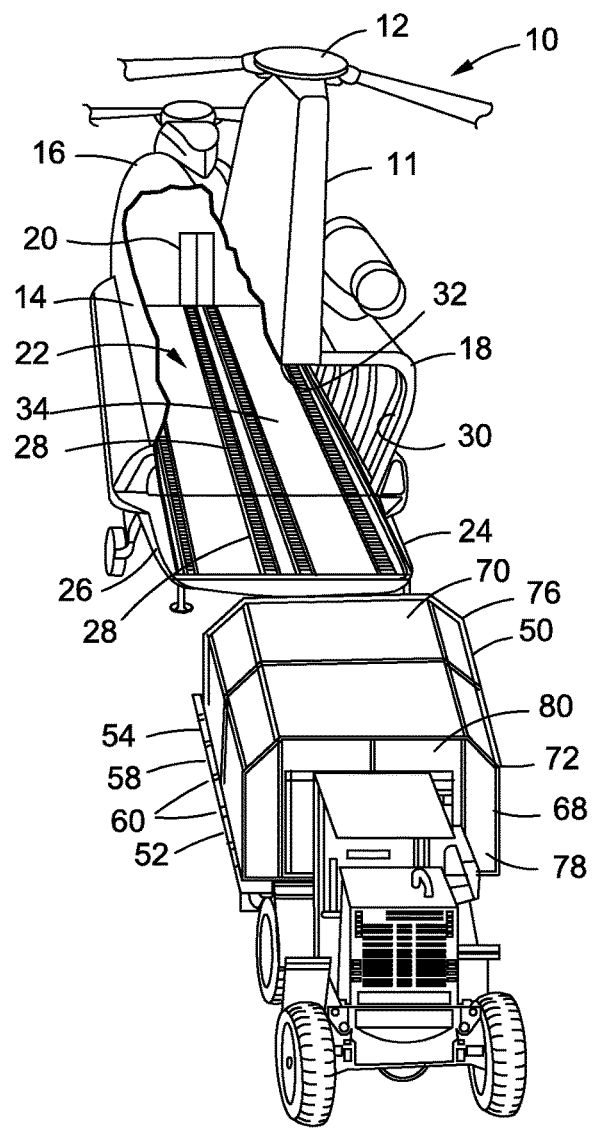
FIG. 3 is an aft perspective illustration of the rotorcraft during loading of a medical pod into the cargo area.

Referring to FIG. 3, shown is an embodiment of a medical pod 50 during loading by a forklift into the cargo area 22 of the rotorcraft 12. As indicated above, the container 72 may be sized and configured to be compatible with the geometry and the internal dimensions of the cargo area 22. For example, the container 72 may have a height that is compatible with the distance between the cargo area floor 34 and ceiling 32 and a width that is compatible with the distance between the cargo area walls 30 of the aircraft. In addition, the container 72 may be configured to be compatible with the internal cargo handling system of a vehicle such as an aircraft 11. For example, the internal cargo handling system may include a roller system 28 which may be incorporated into the cargo door 24/cargo ramp 26 and/or into the cargo area floor 34 to allow for loading and unloading of the container 72 along the roller system 28. In this regard, the roller system 28 may be compatible with the pallet 52 of the container 72.

Referring to FIGS. 4-5, shown is an embodiment of the container 72 in FIG. 4 illustrating the general arrangement of the pallet, the pod side walls 68, the roof section 70, and/or the doors 80 of the container 72. The pallet 52 may have an upper surface 64 which may define a floor structure 62. A transport system 100 may be mounted to the floor structure 62 and may comprise a track system 102. The track system 102 may be integrated or mounted to the floor structure 62 (FIG. 8) to allow for securing the patient restraint system 150 and the seats 200 to the floor structure 62 as is described in greater detail below. The pod side walls 68 may be mechanically fastened (e.g., welded, bolted, bonded, etc.) to the pallet 52 and may extend upwardly to the roof section 70. The pod side walls 68 may be formed of a lightweight structural material such as aluminum or other metallic or nonmetallic material. The container 72 may include reinforcements 84 at the corners of the container 72 and at other areas of the container 72 such as midway along the pod side walls 68. The doors 80 may be hingedly coupled to the container 72 and may be located at the pod forward end 76 and/or at the pod aft end 78 as indicated above.

In FIG. 5, the pallet 52 may comprise a standardized configuration as mentioned above. For example, the pallet 52 may comprise a standardized pallet having a U.S. military designation of 463L. The pallet 52 footprint may be defined by a pallet length 54 and a pallet width 56 of 108 and 88 inches, respectively. The pallet 52 may have a thickness of approximately 2.25 inches although the pallet 52 may be provided in any thickness and in any length and width. Advantageously, when the pallet 52 is oriented lengthwise as shown in FIG. 3, the pallet 52 may be compatible with the cargo handling system of the rotorcraft 12 cargo area 22. When the pallet 52 is oriented widthwise (not shown), the pallet 52 may be compatible with the cargo handling system of certain other cargo aircraft (not shown) such as certain fixed-wing cargo aircraft.

In FIG. 5, the pallet 52 may have a sandwich construction comprising a pair of face sheets (not shown) such as aluminum face sheets and a core (not shown) interposed between the face sheets. The core material may comprise any suitable material including, but not limited to, balsa wood, foam, honeycomb, or any other metallic or nonmetallic core material. However, the pallet 52 is not limited to sandwich construction and may be formed in any configuration including monocoque construction, a homogenous plate, or in other construction configurations. Advantageously, the pallet 52 may include side rails 58 extending along the length and width of the pallet 52. The side rails 58 may include detents or notches 60 at uniformly spaced intervals for accepting or receiving standardized rail locks (not shown) that may be included in the cargo handling system of a given aircraft or other vehicle. The engagement of the rail locks with the side rails 58 may secure the container 72 (FIG. 2) to the aircraft 11 and prevent relative movement. The side rails 58 may also include a plurality of tie-down rings (not shown) located within the notches 60 for securing the container 72 to the aircraft 11.

The pallet 52 may also include one or more drains 86 (FIG. 4) for collecting fluids. Although shown as being mounted at the center of the pallet 52, the drain 86 may be positioned at any location on the pallet 52. The drain 86 may include a valve (not shown) for controlling the discharge of fluids from within the container 72 (FIG. 4) to the outside of the container 72. The drain 86 may be maintained in a closed position when the medical pod 50 is loaded in an aircraft 11. The drain 86 may be opened at any time such as during cleaning of the medical pod 50. For example, a drain hose (not shown) may be coupled to the drain 86 while the medical pod 50 is loaded in the aircraft 11 and the drain 86 may be opened to allow for discharge of fluids. Alternatively, the drain 86 may be opened after the medical pod 50 is removed from the aircraft 11 to allow for discharge of any fluids in the container 72.

Although the medical pod 50 (FIG. 4) and container 72 (FIG. 4) are described in the context of being loaded in the cargo area 22 (FIG. 3) of a rotorcraft 12 (FIG. 3), the medical pod 50 may be sized and configured to be compatible with any type of aircraft 11 and is not limited to the cargo area 22 of a rotorcraft 12. Further in this regard, the medical pod 50 as disclosed herein may be implemented for use in any vehicular or non-vehicular application, and is not limited to aircraft 11. Even further, the medical pod 50 is not limited to medical applications. For example, the medical pod 50 may be configured for use in non-medical applications such as in command, control, reconnaissance, surveillance, and/or transport of high-profile individuals as described below, or in any one of a variety of other applications, without limitation.

Figure 6:
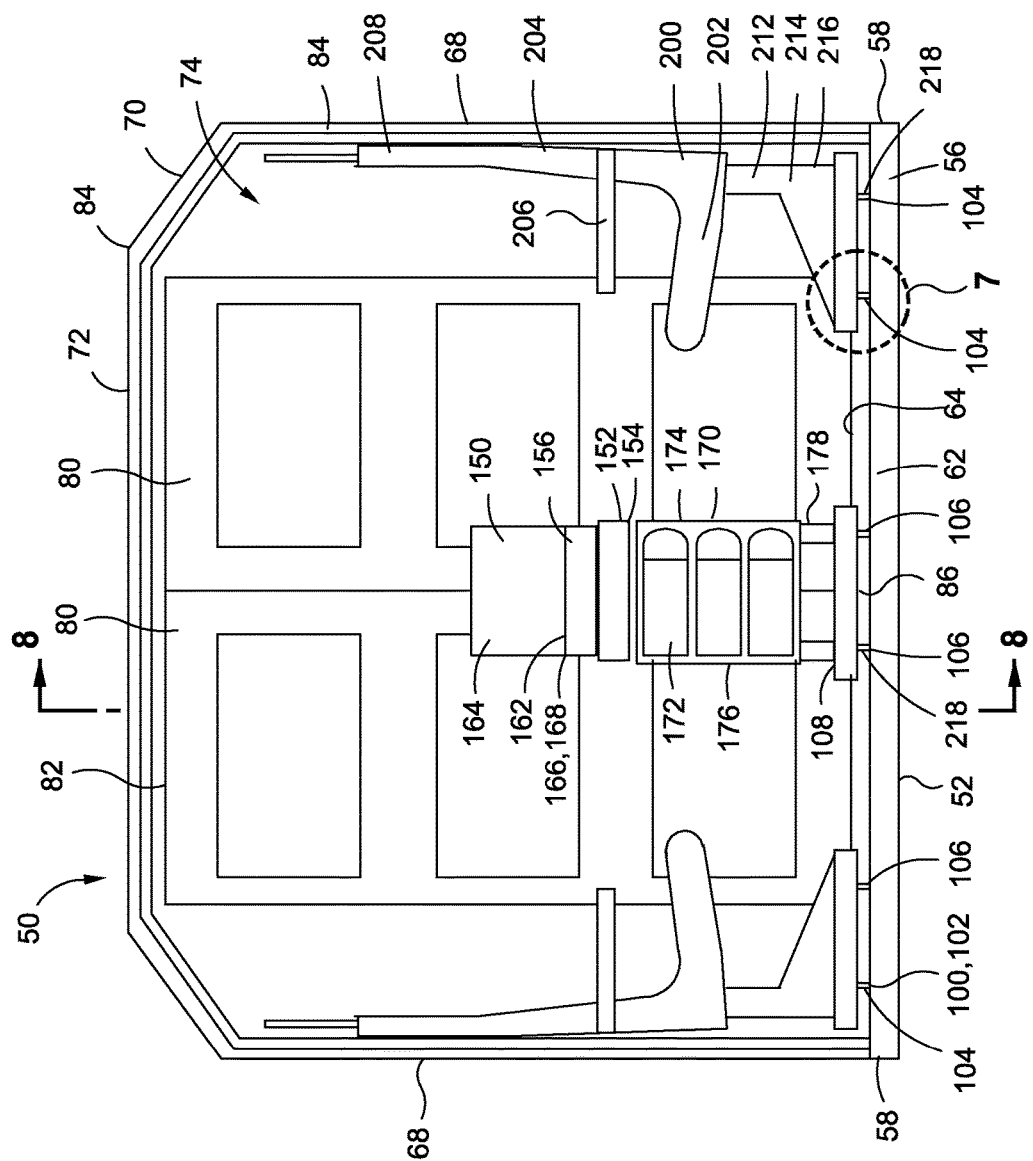
FIG. 6 is an end view of the container.

FIG. 6 is an end view of the medical pod 50 illustrating an arrangement of the seats 200 and the patient restraint system 150 within the container interior 74. In the embodiment shown, the medical pod 50 includes seats 200 on opposing sides of the container 72 with the patient restraint system 150 located between the seats 200. However, as is described in greater detail below, the medical pod 50 may be provided in any one of a variety of configurations and is not limited to the arrangement shown in FIG. 6. FIG. 6 also illustrates the transport system 100 located on or mounted to the floor structure 62. The transport system 100 may facilitate movement of the patient restraint system 150 and/or movement of the seats 200 relative to the floor structure 62 while the patient restraint system 150 and the seats 200 remain coupled to the floor structure 62. Advantageously, the patient restraint system 150 and the seats 200 may be lockable in a given position and/or in a given orientation. In an embodiment, the transport system 100 may comprise a track system 102 including a plurality of seat tracks 104 and a plurality of patient restraint system tracks 106 mounted to, integrated with, or otherwise attached to the floor structure 62. In an embodiment, the track system 102 may be integrated into the floor structure 62 below or substantially flush with the upper surface 64 to prevent the track system 102 from protruding above the upper surface 64 and which may avoid individuals tripping over the track system 102. However, the track system 102 may extend above but preferably below flush with the upper surface 64. The patient restraint system 150 and the seats 200 may include track engagement fittings 218 for engaging the track system 102.

Figure 7:
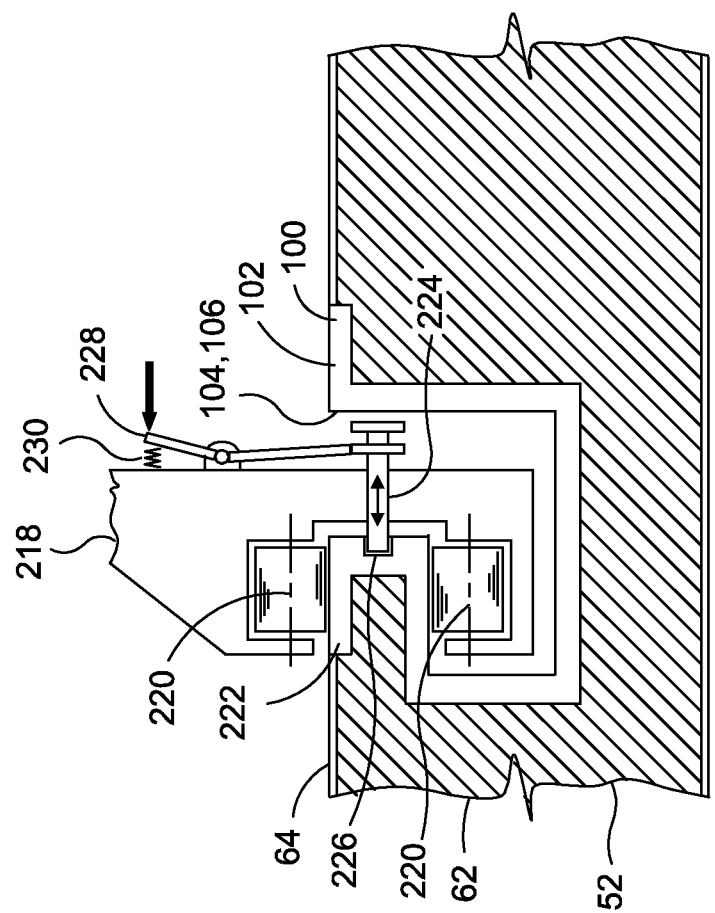
FIG. 7 is a cross-sectional view of a track engagement fitting in an embodiment.

FIG. 7 is a cross-sectional illustration of a non-limiting embodiment of a track engagement fitting 218 as may be included with the patient restraint system 150 and/or the seats 200 (FIG. 6). It should be noted that the embodiment of the track engagement fitting 218 shown in FIG. 7 is one of a variety of different configurations that may be provided for coupling the patient restraint system 150 and/or the seats 200 to the floor structure 62. In the embodiment shown, the track engagement fitting 218 may include upper and lower rollers 220 for engaging a track frame 222 that may be integrated with or mounted to the floor structure 62 of the pallet 52. The upper and lowers rollers 220 may couple the track engagement fitting 218 to the track system 102 and prevent movement of the tracked engagement fitting in a vertical direction relative to the pallet 52.

In FIG. 7, one or more of the track engagement fittings 218 may include a locking mechanism for locking the track engagement fitting 218 to a desired location along the track system 102. In an embodiment, the track system 102 may include a plurality of bores 226 which may be formed in the track frame 222 at spaced intervals. Each one of the bores 226 may be sized and configured to receive a pin 224 which may be slidable within a lateral hole in the track fitting. The engagement of the pin 224 into the bore 226 may positively lock the track engagement fitting 218 to the track system 102 at a given location along the track system 102 and may prevent movement of the seat 200 (FIG. 6) or patient restraint system 150. The pin 224 may be disengaged from the bore by applying pressure to a spring-loaded 230 lever 228 which may be pivotably coupled to the track engagement fitting 218. However, the track engagement fitting 218 may be locked to the track system 102 using any one of a variety of different locking mechanisms and is not limited to the arrangement shown.

In FIG. 6, each one of the seats 200 may be coupled to the pallet 52 by one or more track engagement fittings 218 engaging parallel sets of seat tracks 104 located on each side of the container interior 74 as shown in phantom lines in FIG. 4. The seat tracks 104 may be generally oriented along a lengthwise direction of the container 72 although the seat tracks 104 may be oriented in any direction. Likewise, the patient restraint system 150 may also be coupled to the pallet 52 by one or more track engagement fittings 218 for engaging parallel sets of patent restraint system tracks 106 located along a general center of the container interior 74 and extending generally along a longitudinal direction and a lateral direction of the container 72. However, the pallet 52 may include patient restraint system tracks 106 and seat tracks 104 that may be installed or mounted at any location on the floor structure 62 and in any orientation such that the tracks 106, 104 are not limited to the locations and orientations shown in FIG. 5. In addition, the spacing between the parallel sets of the seat tracks 104 may be the same or different than spacing between the parallel sets of patient restraint system tracks 106.

In FIG. 8, shown is a side sectional view of the medical pod 50 illustrating the patient restraint system 150 and a pair of the seats 200 positioned at opposite ends 76, 78 of the container 72. Each seat 200 may include a headrest 208, a backrest 204, and a seat bottom 202 which may be mounted to a vertical seat frame 216. Each seat 200 may be vertically-height adjustable to fit individuals of different heights. The seats 200 may be lockable in a desired orientation as described below. Each one of the seats 200 may include a seat support base 214 or a seat support structure 212 for supporting the seat 200. A lower end of each seat support structure 212 may include one or more track engagement fittings 218 coupled to the track system 102. The seat support structure 212 may optionally include a rotating base 108 to allow for rotation of the seat 200 such that an occupant may change the orientation of the seat 200 as described below. For example, the seats 200 may be rotatable about a vertical axis (not shown) so that the seats 200 are forward or aft facing for takeoff and landing of an aircraft and side facing when treating a patient. The rotating base 108 may be lockable to lock the seat 200 into a desired seat orientation.

The patient restraint system 150 may include a patient support structure 152 for structural support of the patient restraint system 150. A lower end of the patient support structure 152 may include one or more of the track engagement fittings 218 which may be coupled to the track system 102 as described above. The patient support structure 152 may also include a rotating base 108 to allow for swiveling or rotation of the patient restraint system 150 about a vertical axis (not shown) so that medical personnel may orient the patient restraint system 150 for optimal access to a desired location on the patient's body. The rotating base 108 may be lockable such that the patient restraint system 150 may be locked into any orientation. The patient restraint system 150 may include a patient table 154 which may comprise a head portion 164, a torso portion 166, and a leg portion 168. The patient table 154 may be covered by a pad 156 for cushioning support the patient. The patient table 154 may be articulated at one or more locations. For example, the torso portion 166 may be pivoted upwardly at an angle 190 relative to the leg portion 168. Other areas of the patient table 154 may be articulated. The patient may be secured to the patient table 154 by one or more straps 162 (FIG. 9) or safety belts that may be mounted at one or more locations along the patient table 154 to prevent movement of the patient during vehicle movement.

Figure 9:
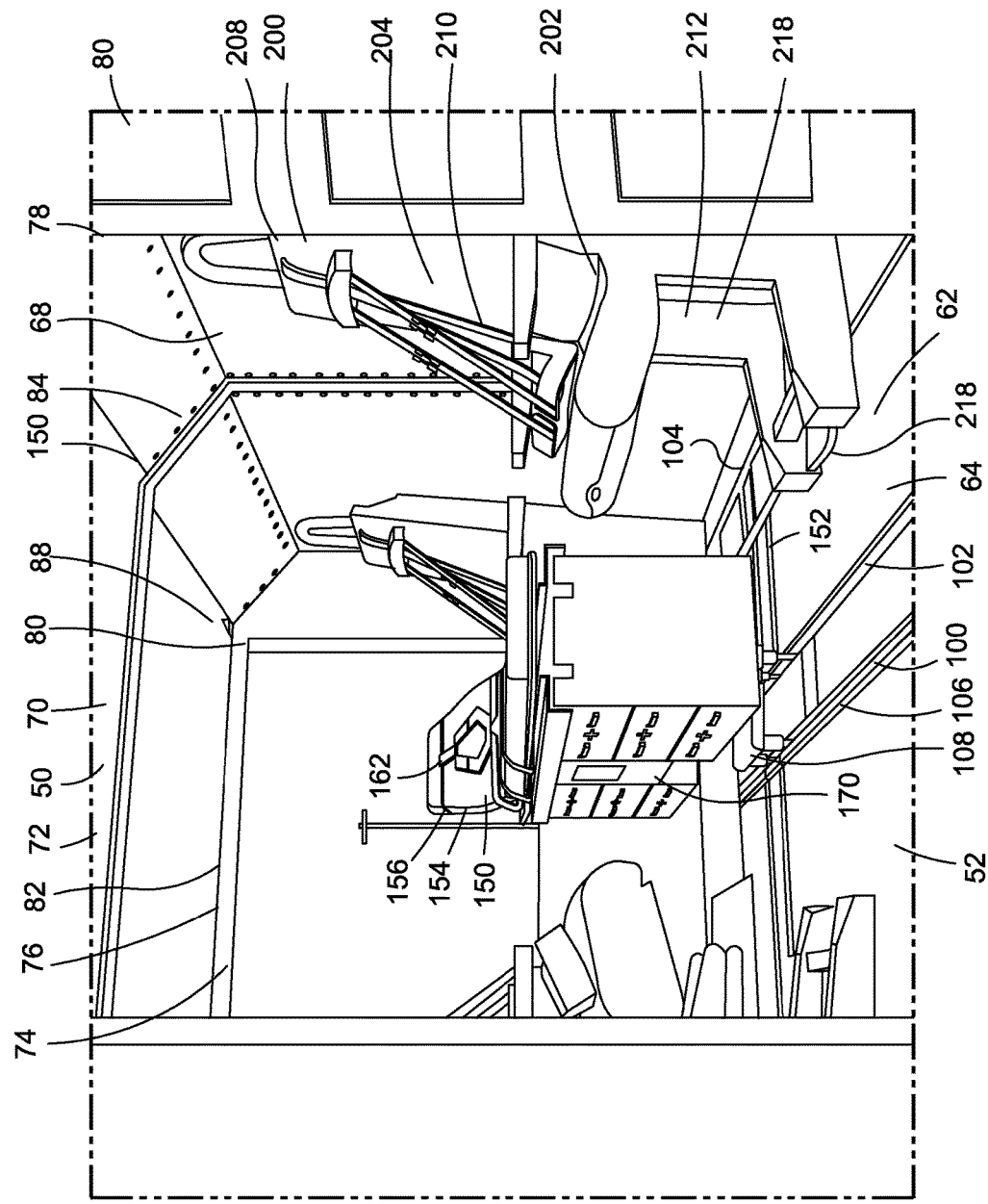
FIG. 9 is a perspective illustration of the container interior showing a patient restraint system and a plurality of seats that may be coupled to the pallet.

In FIG. 9, shown is a perspective illustration of the container interior 74. Each one of the seats 200 may include a seatbelt and/or harness 210 for restraining the occupant of the seat 200. Advantageously, the harness 210 may be configured to engage an occupant and allow the occupant to sit or stand while remaining secured to the harness 210. The harness 210 may be coupled to a restraint mechanism (not shown) such as an inertial locking mechanism (not shown) to prevent harmful movement of the occupant that may result from rapid accelerations due to turbulence, abrupt maneuvers, a hard landing, or other types of rapid movement of the aircraft 11 (FIG. 3) or vehicle. The harness 210 may also be coupled to a pretensioner (not shown) to provide a limited amount of tension in the harness 210 to prevent jerking of the occupant against the harness 210 during an acceleration or deceleration event. In this regard, the harness 210 may prevent harmful impact of an occupant with the elements (e.g., the seats 200, the patient restraint system 150) inside the container interior 74 or harmful impact with other occupants (e.g., the patient, other medical personnel) inside the container 72.

FIG. 9 also illustrates the transport system 100 or track system 102 that may be integrated with or mounted to the floor structure 62. In the embodiment shown, the patient restraint system tracks 106 are oriented along a generally longitudinal direction 90 and along a generally lateral direction 92 (FIG. 12) of the container to form a cross shape. In the embodiment shown, the track system 102 for the patient restraint system 150 may extend in a longitudinal direction 90 all the way to the aft end 78 of the container 72 which may facilitate loading of a patient onto the patient restraint system 150 as described below. The track system 102 for the patient restraint system 150 also extends along a lateral direction 92 so that the patient may be moved closer to the pod side walls 68 to allow for easier access to the patient by medical personnel.

Figure 10:
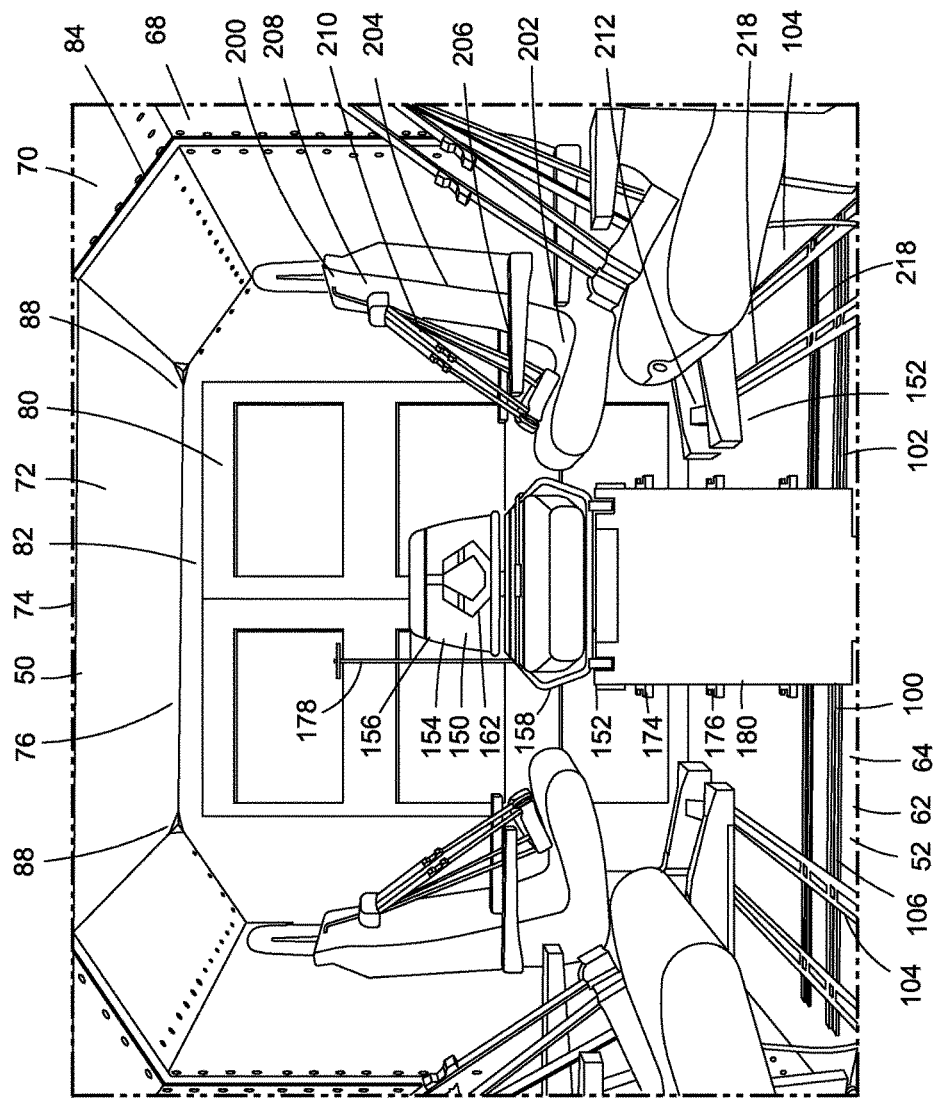
FIG. 10 is a further perspective illustration of the container interior and illustrating the engagement of the patient restraint system and the seats to the pallet by means of a plurality of tracks mounted to the pallet.

FIG. 10 is an end view of the container interior 74 illustrating an embodiment of the track system 102 mounted to or integrated with the floor structure 62. The container 72 may include one or more lighting fixtures 88 which may be mounted at strategic locations within the container interior 74 such as an interior of the roof section 70 to provide lighting for the medical personnel treating the patient. In an embodiment, the lighting system may be powered by a suitable power source 180 such as by battery power which may be included with the medical pod 50. For example, the patient support structure 152 may include provisions for mounting one or more batteries for powering the lighting system and/or for powering medical equipment 170 such that the medical pod 50 may be operated as a self-contained unit. However, it is contemplated that the medical pod 50 may be configured to be connectable to the electrical power system of the vehicle. Although not shown, the medical pod 50 may also include one or more of ventilation ports and/or the ventilation fans for circulating fresh air through the container interior 74.

Figure 11:
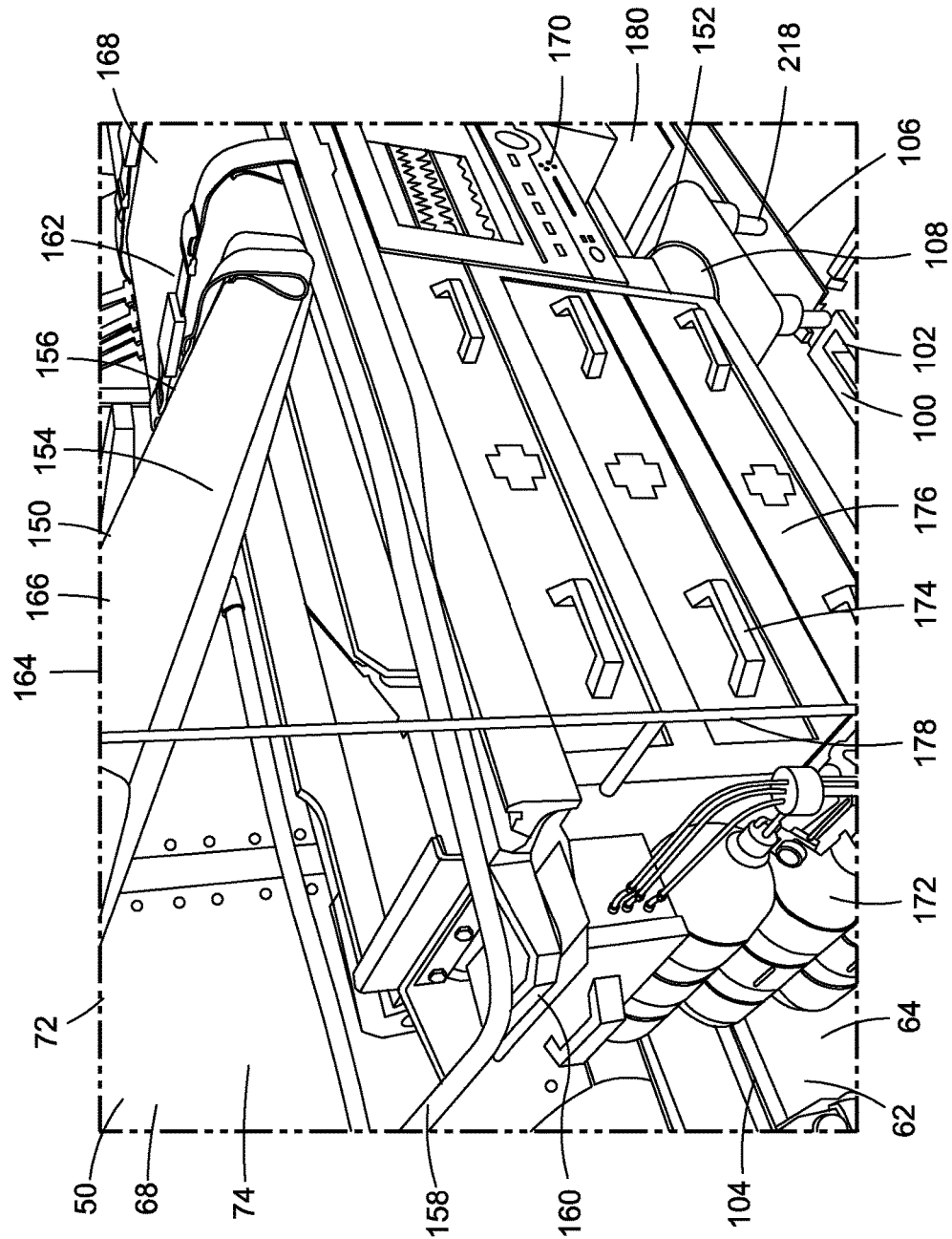
FIG. 11 is a perspective illustration of the patient restraint system including a padded platform or table for supporting the patient and further including medical equipment for treating the patient.

FIG. 11 is a perspective illustration of the patient restraint system 150. The torso portion 166 of the patient table 154 is shown in an elevated position. That patient restraint system 150 may include a railing 158 which may extend around the perimeter of the patient table 154 to allow medical personnel to maneuver the patient restraint system 150. In this regard, one or more handles 160 may be provided on one or more ends of the patient restraint system 150. Advantageously, specialized medical equipment 170 may be mounted to the patient restraint system 150. For example, oxygen bottles 172, an intravenous pole 178, an EKG monitor, and various medical supplies 176 may be included with the patient restraint system 150. For example, although not shown, the patient restraint system 150 may include devices such as a defibrillator, a ventilator, a pulse oximeter, and various other devices such as suction pumps, air pumps, infusion pumps, and other devices, without limitation. The patient restraint system 150 may also include a plurality of drawers 174 containing various medical supplies 176 such as surgical gloves, masks, bandages, hand instruments, and other supplies.

FIG. 12 is a schematic top view of an embodiment of the medical pod 50 as may be mounted in a cargo area 22 of a vehicle 10 such as an aircraft 11. As can be seen, the medical pod 50 may be oriented in a lengthwise direction within the cargo area 22. The medical pod 50 may be sized and configured complementary to a width of the cargo area 22 such that the pod side walls 68 are in relatively close proximity to the cargo area walls 30 and the doors 80 are located at forward and aft ends 76, 78 of the medical pod 50. FIG. 12 further illustrates the seats 200 in a first seat position 250 and a first seat orientation 254. For example, the seats 200 may be oriented in a forward/aft facing direction as may be desired during takeoff and/or landing of the aircraft 11. The patient restraint system 150 is shown in a first position 182 at a general center of the container 72. However, the patient restraint system 150 is movable along the track system 102 in a lateral direction 92 and/or in a longitudinal direction 90 to different positions within the container 72. Furthermore, although shown in a first orientation 186 generally parallel to a longitudinal direction 90 of the container 72, the patient restraint system 150 may be rotated about a vertical axis (not shown) into one or more orientations as described below. Even further, the patient restraint system 150 may be tilted (not shown) from a relatively horizontal orientation as shown in FIG. 8 to a tilted position (not shown) wherein the patient's head may be at a higher level than the patient's feet, or vice versa.

FIG. 13 a schematic top view of the medical pod 50 showing the patient restraint system 150 translated along the track system 102 in a longitudinal direction 90 (FIG. 12) from a first position 182 (FIG. 12) to a second position 184 adjacent the pod aft end 78. In addition, the seats 200 at the pod aft end 78 have been moved from a first seat position 250 at the pod aft end 78 to a second seat position 252 adjacent the seats 200 at the pod forward end 76. In the positions shown in FIG. 12, the patient restraint system 150 extends outside of the container 72 while the patient restraint system 150 remains attached to the track system 102. By extending the patient restraint system 150 at least partially outside of the container 72, loading and unloading of the patient from the medical pod 50 may be performed with greater convenience. For example a new patient may be carried on a stretcher to the medical pod 50. With the doors 80 open 82, one or more personnel located inside the container 72 may help lift the stretcher and patient onto the patient restraint system 150. The patient may be secured to the patient restraint system 150 by the straps 162 (FIG. 11). The patient restraint system 150 may then be translated back toward the center of the container and locked into position prior to movement of the vehicle. In addition, in a contemplated embodiment, not shown, the track system 102 (e.g., patient restraint system tracks 106) may extend to a perimeter of each of the forward and aft ends 76, 78 providing an ability to extend the patient restraint system 150 out of either end 76, 78 of the medical pod 50.

FIG. 14 is a schematic top view of the medical pod 50 showing the patient restraint system 150 translated along the track system 102 in a lateral direction 92 toward the side of the container 72. In addition, the seats 200 may be moved back to the pod forward end 76 and the pod aft end 78. The seats 200 on one side (e.g., right-hand side) of the container 72 may be moved into a folded configuration. In this regard, the seat bottoms 202 and/or armrests 206 (not shown) of any of the seats 200 may be movable between stowed and deployed positions. The folding of the seat bottoms 202 and the translation of the patient restraint system 150 toward the side of the container 72 shown in FIG. 14 may provide a passageway 258 to allow personnel (e.g., the flight crew) to pass through the medical pod 50 from one end to an opposite end. Movement of personnel between the aircraft aft end 18 and the aircraft forward end 16 may be otherwise unavailable due to the close-fitting arrangement of the pod side walls 68 with the cargo area walls 30.

FIG. 15 is a schematic top view of the medical pod 50 showing the patient restraint system 150 rotated about a vertical axis from a first orientation 186 (FIG. 12) to a second orientation 188 wherein the patient restraint system 150 is located at an angle 190 (FIG. 15) relative to a longitudinal direction 90 (FIG. 12) of the container. Also in FIG. 15, each one of the seats 200 has been moved from a first seat position 250 (FIG. 12) adjacent the pod forward end 76 and pod aft end 78 to a position midway between the pod forward end 76 and pod aft end 78. The patient restraint system 150 is rotatable using the rotating base 108 shown in FIG. 8. Advantageously, by maneuvering the patient restraint system 150 into a desired orientation and position and by translating the seats 200 adjacent to a desired location near the patient restraint system 150, medical personnel may have access to the patient while seated in their seats 200.

FIG. 16 is a schematic top view of the medical pod 50 wherein the seats 200 on the left-hand side of the container 72 have been translated toward the pod forward end 76. The seats 200 on the right hand side have been translated toward the pod aft end 78. In addition, the patient restraint system 150 has been rotated from an orientation substantially parallel to the longitudinal direction 90 (FIG. 12) to an orientation of less than approximately 45 degrees to the longitudinal direction 90. Advantageously, the patient restraint system 150 is configured to enable rotation of the patient such that any area of the patient's body may be physically accessible to the medical personnel.

FIG. 17 is a schematic top view of the medical pod 50 in an alternative medical configuration 300 wherein the patient restraint system 150 is omitted. A stack of stretchers 302 may be mounted to the pod sidewall 68 in a wall-mounted 304 configuration. For example, the container 72 may be configured to support up to four (4) or more stretchers 302 stacked one on top of the other on one or both sides of the container 72. An opposite side of the container 72 may include a plurality of seats 200 which may be coupled to the floor structure 62. The seats 200 may be translatable and rotatable in the manner described above.

Figure 18:
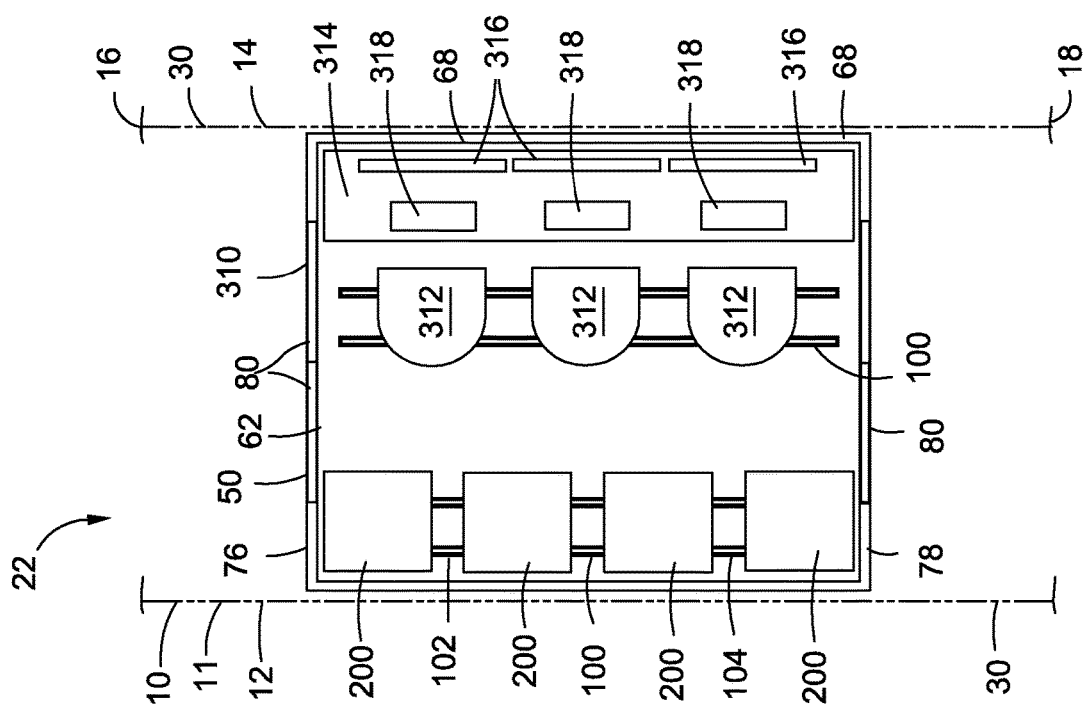
FIG. 18 is a top schematic view of a non-medical configuration of the container having a plurality of workstations and a plurality of seats.

FIG. 18 is a schematic top view of a container 72 in a non-medical configuration 310. In the arrangement shown, the patient restraint system 150 may be omitted. A plurality of work stations 312 may be installed on one side of the container 72. Each work station 312 may include a computer with a seat for the operator of the computer. A console 314 may be mounted to the pod side wall 68 or on the floor structure 62 for supporting a plurality of user interfaces 318 (e.g., keyboards) and monitors or displays 316 for the workstations. The container 72 may include a plurality of seats 200 which may be coupled to the floor structure 62 such that the seats 200 are translatable and rotatable in a manner described above. The non-medical configuration 310 illustrated in FIG. 18 may be outfitted for various non-medical operations such as command and control, reconnaissance, surveillance, search and rescue, and other non-medical operations.

Figure 19:
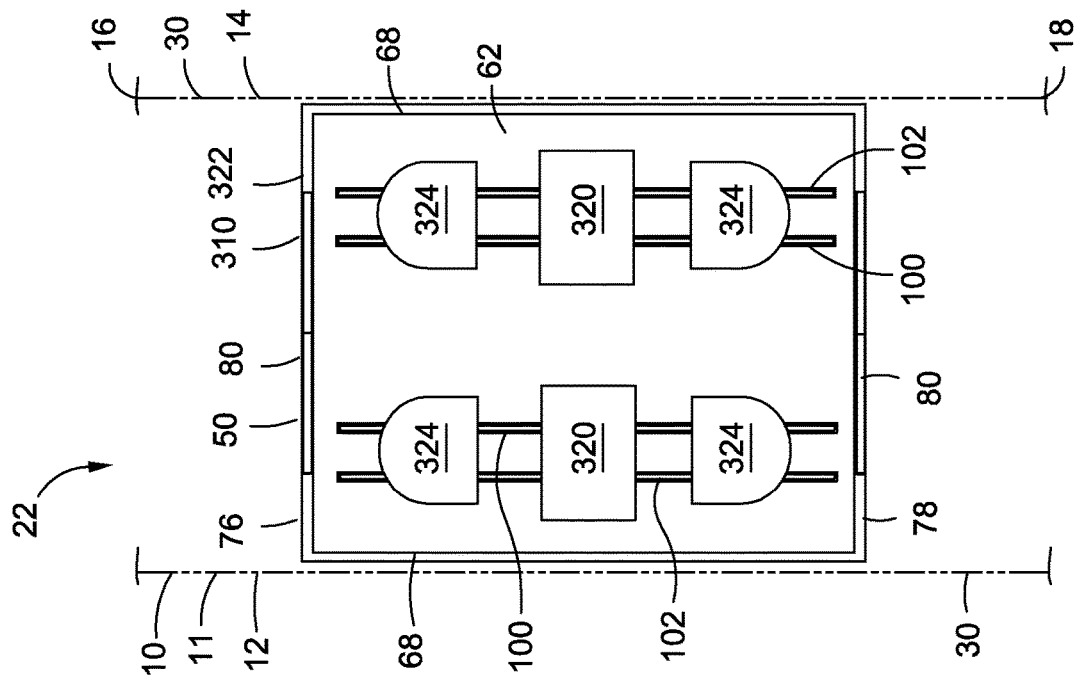
FIG. 19 is a top schematic view of a further non-medical configuration of the container including passenger seats for secure passenger transport.

FIG. 19 is a schematic top view of a further non-medical configuration 310 of the container 72. The container 72 may be configured for secure passenger transport 322 for transporting high-profile individuals such as heads of state in a quiet and secure environment on a cargo aircraft 11. The passenger seats 324 may be coupled to the floor structure 62 by means of the track system 102 as disclosed above. One or more tables 320 may also be attached to the floor structure 62 by means of the track system 102. In an embodiment, the container 72 for transporting high-profile individuals or any of the other embodiments disclosed above may optionally include ballistic protection underneath the floor structure 62 and/or on an exterior of the pod side walls 68. Such ballistic protection may comprise ballistic-resistant panels that may be attached to or integrated with the floor structure 62 and/or the pod side walls 68.

Figure 20:
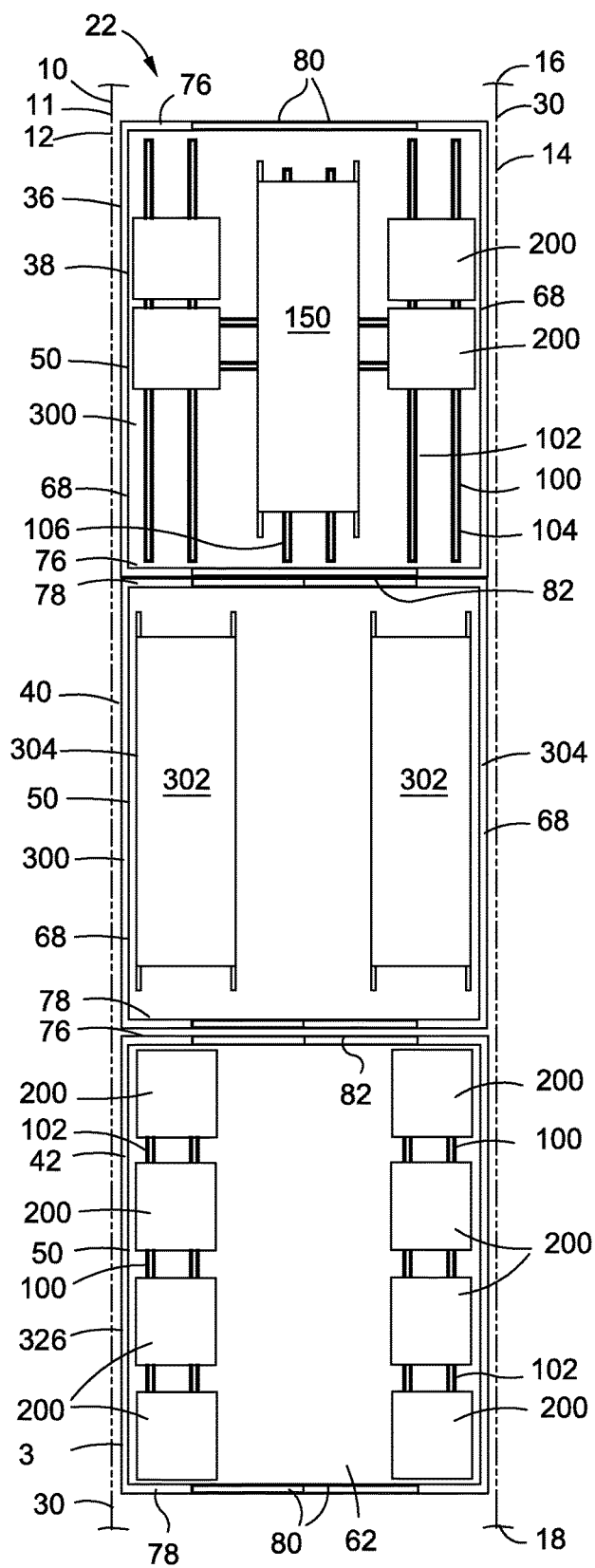
FIG. 20 is a top schematic view of a plurality of different pod configurations arranged end-to-end in a cargo area of an aircraft.

FIG. 20 is a schematic top view of an end-to-end arrangement of a plurality of the pods within a cargo area 22 of a vehicle 10 such as the rotorcraft 12 illustrated in FIG. 2. In the embodiment shown, a pair of medical pods 50 may be installed in first and second pallet positions 38, 40 of the cargo area 22 of the rotorcraft 12 of FIG. 2. The medical pod 50 located in the first pallet position 38 may be located toward a forward end 16 of the aircraft 11 and may include a patient restraint system 150 for a patient and a plurality of seats 200 for medical personnel. The medical pod 50 located in the second pallet position 40 may be outfitted with stretchers 302 stacked up in a wall-mounted 304 configuration as described above. For example, each one of the pod side walls 68 may be configured to support a plurality of stretchers 302 containing patients. A non-medical pod 50 may be located in a third pallet position 42 of the cargo area 22 toward the aft end 18 of the rotorcraft 12 and may contain a security detail 326 or other non-medical personnel.

Figure 21:
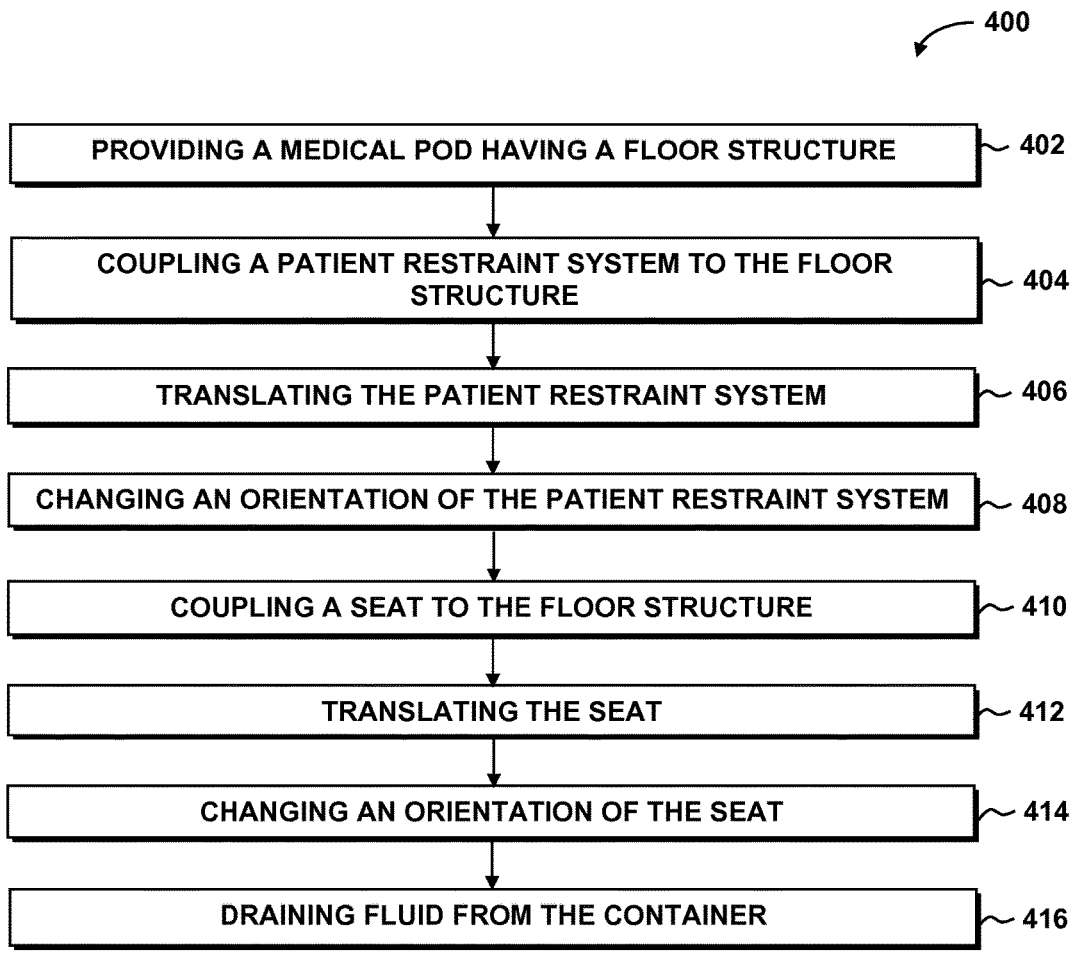
FIG. 21 is a flow diagram having one or more operations that may be included in a method of transporting the patient.

FIG. 21 illustrates a method 400 for transporting a patient by using the medical pod 50 or transporting other personnel using the container 72 in a non-medical configuration 300 as disclosed herein.

Step 402 of the method 400 of transporting a patient may include providing a medical pod 50 (FIG. 12) having a pallet 52 (FIG. 12) forming a floor structure 62 (FIG. 12) of the container 72 (FIG. 12). The medical pod 50 may include pod side walls 68 (FIG. 12) that extend upwardly from the pallet 52 to a roof section 70 (FIG. 12). The medical pod 50 may include one or more doors 80 (FIG. 12) located on a pod forward end 76 (FIG. 12) and/or a pod aft end 78 (FIG. 12) of the medical pod 50. The medical pod 50 may be loaded into a vehicle 10 such as through a cargo door 24 and into a cargo area 22 of an aircraft 11 such as is shown in FIGS. 2-3.

Step 404 of the method 400 of FIG. 21 may include coupling a patient restraint system 150 (FIG. 12) to the floor structure 62 (FIG. 12) using a transport system 100 or a track system 102 (FIG. 12). As was described above, the track system 102 may be located on the floor structure 62 or otherwise integrated with or mounted to the floor structure 62 of the pallet 52 (FIG. 12). For example, FIG. 7 illustrates an embodiment of a track engagement fitting 218 that may be implemented for attaching one or more of the seats 200 and/or the patient restraint system 150 to the track system 102 of the floor structure 62.

Step 406 of the method 400 of FIG. 21 may include translating the patient restraint system 150 from a first position 182 to a second position 184 using the transport system 100. For example, FIG. 12 illustrates the patient restraint system 150 located in a first position 182 toward a center of the container 72. FIG. 13 illustrates translation of the patient restraint system 150 using the track system 102 in a longitudinal direction 90 (FIG. 12) toward an aft end of the container 72.

Step 408 of the method 400 of FIG. 21 may include changing an orientation of the patient restraint system 150. For example, FIG. 12 illustrates the patient restraint system 150 in a first orientation 186 relative to the container 72. FIG. 16 illustrates rotation of the patient restraint system 150 about a vertical axis (not shown) to an angle 190 relative to a longitudinal direction 90 of the container.

Step 410 of the method 400 of FIG. 21 may include coupling a seat 200 to the floor structure 62. FIG. 7 illustrates the coupling of one of the seats 200 (FIG. 6) to the floor structure 62 by means of the track engagement fittings 218 placed in engagement with the track system 102. In the embodiment shown, the track engagement fitting 218 may include one or more mechanisms for preventing vertical movement of the track engagement fitting 218 relative to the floor structure 62. Although not shown, the track engagement fitting 218 may also include one or more mechanisms for preventing lateral movement of the track engagement fitting 218 relative to the floor structure 62.

Step 412 of the method 400 of FIG. 21 may include translating the seat 200 from a first seat position 250 to a second seat position 252 within the container 72. For example, FIG. 12 illustrates two (2) of the seats 200 located in a first seat position 250 adjacent the pod aft end 78 of the container 72. FIG. 13 illustrates translation of the seats 200 using the track system 102 along a longitudinal direction 90 to a second seat position 252 adjacent to the pod forward end 76 of the container 72.

Step 414 of the method 400 of FIG. 21 may include changing an orientation of the seat 200 from a first seat orientation 254 to a second seat orientation 256. For example, FIG. 12 illustrates the seats 200 which may be oriented in a forward facing direction and/or an aft facing direction as may be required during takeoff and/or landing of an aircraft 11. FIG. 15 illustrates rotation of the seats 200 into a second seat orientation 256 wherein the seats 200 may be oriented in a side facing direction as may be desired by medical personnel when treating the patient.

Step 416 of the method 400 of FIG. 21 may include draining fluid from the container 72 such as by using a drain 86 (FIG. 4) which may be integrated into or mounted to the floor structure 62 (FIG. 4) of the pallet 52 (FIG. 4). As was indicated above, one or more drains 86 may be provided with the medical pod 50 for collecting and containing fluids in the container 72 (FIG. 4) which may be otherwise hazardous to personnel or hazardous to the aircraft structure. The drain 86 may be maintained in a closed position (not shown) when the medical pod 50 (FIG. 3) is loaded in the aircraft 11 (FIG. 3). When the medical pod 50 has been removed from the aircraft, the drain 86 may be opened to discharge the fluids from the container 72 such as during cleaning of the container 72.

Additional modifications and improvements of the present disclosure may be apparent to those of ordinary skill in the art. Thus, the particular combination of parts described and illustrated herein is intended to represent only certain embodiments of the present disclosure and is not intended to serve as limitations of alternative embodiments or devices within the spirit and scope of the disclosure.

What is claimed is:

1. A method of transporting a patient using a medical pod having a pallet forming a floor structure and including sidewalls extending upwardly from the pallet to a roof section to form an enclosed container, the method comprising the steps of:
coupling a patient restraint system to the floor structure by engaging track engagement fittings to a patient track system having lengthwise tracks extending along a container width and integrated into or directly mounted to the floor structure; translating the patient restraint system in at least one of a lengthwise direction and a widthwise direction relative to the floor structure respectively along the lengthwise tracks and widthwise tracks; and loading the medical pod into a vehicle.

2. The method of claim 1, further comprising the step of:
changing an orientation of the patient restraint system from a first orientation to a second orientation.

3. The method of claim 2, further comprising the step of:
rotating the patient restraint system into an orientation of less than approximately 45 degrees to a longitudinal direction of the container.

4. The method of claim 1, further comprising the step of:
translating the patient restraint system to a position wherein at least a portion of the patient restraint system extends outside of the container.

5. The method of claim 1, further comprising the steps of:
coupling a seat to the floor structure using a seat support structure; and
translating the seat from a first seat position to a second seat position within the container.

6. The method of claim 5, further comprising the step of:
changing an orientation of the seat by rotating the seat.

7. The method of claim 1, further comprising the step of:
draining fluid from the medical pod through a drain mounted to the floor structure.

8. The method of claim 1, wherein:
the vehicle is an aircraft.

9. The method of claim 8, wherein:
the aircraft is one of a rotorcraft and a fixed-wing aircraft.

10. The method of claim 1, wherein the step of loading the medical pod into the vehicle includes:
securing the pallet to the vehicle.

11. The method of claim 1, wherein the vehicle includes a roller system incorporated into a cargo area floor, the step of loading the medical pod into the vehicle includes:
loading the medical pod along the roller system.

12. The method of claim 1, wherein the step of loading the medical pod into the vehicle includes:
orienting the medical pod in a lengthwise direction within the vehicle.

13. The method of claim 1, wherein the medical pod includes a door located on at least one of a forward end and an aft end of the medical pod, the step of loading the medical pod into the vehicle includes:
orienting the medical pod such that the door is facing in at least one of a forward and aft direction of the vehicle.

14. A method of transporting a patient in an aircraft using a medical pod having a pallet forming a floor structure and including sidewalls extending upwardly from the pallet to a roof section to form an enclosed container, the method comprising:
coupling a patient restraint system to the floor structure by engaging track engagement fittings to a patient track system having lengthwise tracks extending along a container length and integrated into or directly mounted to the floor structure, and widthwise tracks extending along a container width and integrated into or directly mounted to the floor structure;
loading the medical pod into an aircraft; and
translating the patient restraint system in at least one of a lengthwise direction and a widthwise direction relative to the floor structure respectively along the lengthwise tracks and widthwise tracks.

15. The method of claim 14, wherein the step of loading the medical pod into an aircraft comprises:
loading the medical pod into one of a rotorcraft and a fixed-wing aircraft.

16. The method of claim 14, wherein the step of loading the medical pod into the aircraft includes:
securing the pallet to a floor of the aircraft.

17. The method of claim 1, wherein the step of coupling the patient restraint system to the floor structure includes:
coupling the patient restraint system to the track system integrated into the floor structure below or substantially flush with the upper surface.

18. The method of claim 1, wherein:
the track system extends between a pod forward end and a pod aft end.

19. The claim 1, further comprising:
  locking the patient restraint system into position prior to movement of the vehicle.

20. The method of claim 5, wherein the step of translating the seat from the first seat position to the second seat position includes:
  translating the seat along seat tracks mounted to or integrated with the floor structure.

* * * * *